United States Patent [19]

Riebel et al.

[11] Patent Number: 5,270,288
[45] Date of Patent: Dec. 14, 1993

[54] HERBICIDAL N-AZINYL-N'-(2-ETHYLSULPHINYL-PHENYLSULPHONYL)-UREAS

[75] Inventors: Hans-Jochem Riebel, Wuppertal; Hans-Joachim Santel, Leverkusen; Klaus Lürssen; Robert R. Schmidt, both of Bergisch Gladbach, all of Fed. Rep. of Germany

[73] Assignee: Bayer Aktiengesellschaft, Leverkusen, Fed. Rep. of Germany

[21] Appl. No.: 919,651

[22] Filed: Jul. 24, 1992

[30] Foreign Application Priority Data

Aug. 9, 1991 [DE] Fed. Rep. of Germany ....... 4126423
Feb. 11, 1992 [DE] Fed. Rep. of Germany ....... 4203875

[51] Int. Cl.$^5$ .................. C07D 239/69; A01N 43/54
[52] U.S. Cl. .................... 504/214; 544/321; 544/332
[58] Field of Search .............. 71/92; 544/321, 332; 504/214

[56] References Cited

U.S. PATENT DOCUMENTS 4,169,719 10/1979 Levitt ........................ 71/92
4,655,822 4/1987 Levitt ........................ 544/321
4,818,277 4/1989 Levitt ........................ 71/92

FOREIGN PATENT DOCUMENTS 0101308 2/1982 European Pat. Off. .
0074282 3/1983 European Pat. Off. .

Primary Examiner—John M. Ford
Attorney, Agent, or Firm—Sprung Horn Kramer & Woods

[57] ABSTRACT

Herbicidal N-azinyl-N'-(2-ethylsulphinyl-phenylsulphonyl)ureas of the formula

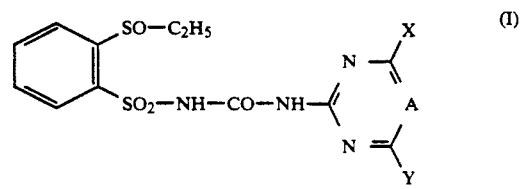

in which
A represents nitrogen or a CH group,
X represents hydrogen, halogen or alkyl, alkoxy or alkylthio, each of which has 1 to 3 carbon atoms and each of which is optionally substituted by halogen and
Y represents alkyl or alkoxy, each of which has 1 to 3 carbon atoms and each of which is optionally substituted by halogen,
and salts thereof.

7 Claims, No Drawings

HERBICIDAL N-AZINYL-N'-(2-ETHYLSULPHINYL-PHENYL-SULPHONYL)-UREAS

The invention relates to new N-azinyl-N'-(2-ethylsulphinyl-phenylsulphonyl)-ureas, processes for their preparation, and their use as herbicides.

It has been disclosed that certain arylsulphonylureas having substituents bonded via sulphur such as, for example, N-(4,6-dimethoxy-s-triazin-2-yl)-N'-(2-propylthio-phenylsulphonyl)-urea (cf. U.S. Pat. No. 4,818,277) or N-(4,6-dimethylpyrimidin-2-yl)-N'-(2-methyl-sulphinylphenylsulphonyl)-urea (cf. U.S. Pat. No. 4,169,719; cf. also EP-A 101,308, EP-A 35,893) have herbicidal properties. However, the herbicidal action of these known compounds is not satisfactory in all respects.

New N-azinyl-N'-(2-ethylsulphinyl-phenylsulphonyl)-ureas of the general formula (I)

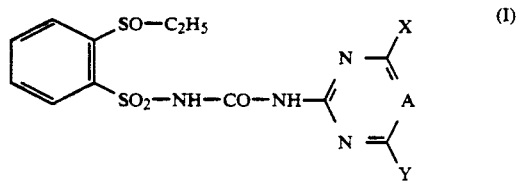

in which
A represents nitrogen or a CH group,
X represents hydrogen, halogen or alkyl, alkoxy or alkylthio, each of which has 1 to 3 carbon atoms and each of which is optionally substituted by halogen and
Y represents alkyl or alkoxy, each of which has 1 to 3 carbon atoms and each of which is optionally substituted by halogen, and salts of compounds of the formula (I) have now been found.

The new N-azinyl-N'-(2-ethylsulphinyl-phenylsulphonyl)ureas of the general formula (I) are obtained when N-azinyl-N'-(2-ethylthio-phenylsulphonyl)-ureas of the general formula (II)

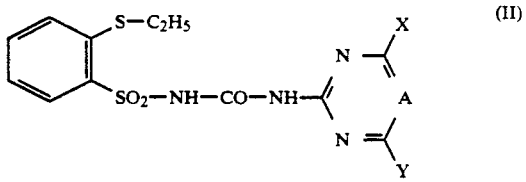

in which
A, X and Y have the abovementioned meanings
are reacted with hydrogen peroxide (H2O2) in the presence of a diluent,
and, if appropriate, the products obtained in this way are converted into salts by customary methods.

The new N-azinyl-N'-(2-ethylsulphinyl-phenylsulphonyl)ureas of the formula (I) are distinguished by a powerful herbicidal activity.

Surprisingly, the new compounds of the formula (I) show a considerably more powerful action than the known compounds N-(4,6-dimethoxy-s-triazin-2-yl)-N'-(2-propylthiophenylsulphonyl)-urea and N-(4,6-dimethylpyrimidin-2-yl)-N'-(2-methylsulphinyl-phenylsulphonyl)-urea, which are comparable in terms of structure and profile of action.

The invention preferably relates to compounds of the formula (I) in which
A represents nitrogen or a CH group,
X represents hydrogen, fluorine, chlorine, bromine, or represents alkyl, alkoxy or alkylthio, each of which has 1 or 2 carbon atoms and each of which is optionally substituted by fluorine and/or chlorine, and
Y represents alkyl or alkoxy, each of which has 1 or 2 carbon atoms and each of which is optionally substituted by fluorine and/or chlorine.

The invention furthermore preferably relates to salts which are obtained from compounds of the formula (I) and bases such as, for example, sodium hydroxide, sodium hydride, sodium amide, sodium carbonate, potassium hydroxide, potassium hydride, potassium amide, potassium carbonate, calcium hydroxide, calcium hydride, calcium amide or calcium carbonate, sodium $C_1$-$C_4$-alkanolates or potassium $C_1$-$C_4$-alkanolates, ammonia, $C_1$-$C_4$-alkylamines, di- ($C_1$-$C_4$-alkyl) -amines or tri- ($C_1$-$C_4$-alkyl) -amines.

The invention particularly relates to compounds of the formula (I) in which
A represents nitrogen or a CH group,
X represents hydrogen, chlorine, methyl, ethyl, methoxy, ethoxy, difluoromethoxy or methylthio and
Y represents methyl, ethyl, trifluoromethyl, methoxy, ethoxy or difluoromethoxy.

If, for example, N-(4,6-dimethoxy-pyrimidin-2-yl)-N'-(2-ethylthio-phenylsulphonyl)-urea is used as starting substance, the course of the reaction can be outlined by the following equation:

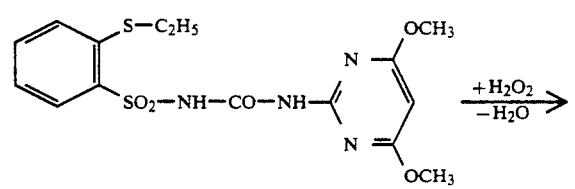

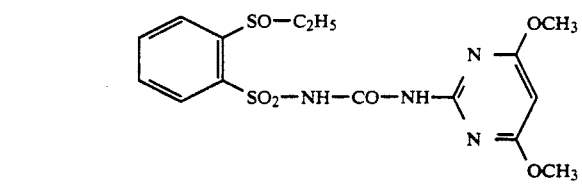

Formula (II) provides a general definition of the N-azinyl-N'-(2-ethylthio-phenylsulphonyl)-ureas to be used as starting substances in the process according to the invention for the preparation of compounds of the formula (i).

In formula (II), A, X and Y preferably, or in particular, have those meanings which have already been mentioned above in connection with the description of the compounds of the formula (I) according to the invention as being preferred, or particularly preferred, for A, X and Y.

The starting substances of the formula (II) are known and/or can be prepared by processes known per se (cf. U.S. Pat. No. 4,127,405, U.S. Pat. No. 4,169,719).

The process according to the invention is carried out using hydrogen peroxide. The hydrogen peroxide is preferably employed as an aqueous solution which preferably contains between 5% and 55%, in particular between 10% and 50%, of $H_2O_2$.

The process according to the invention is carried out in the presence of a diluent. Diluents which are suitable for this purpose are virtually all those which are customary in oxidation reactions. Diluents which are preferred for the process according to the invention are carboxylic acids such as formic acid, acetic acid and propionic acid, in particular acetic acid.

When carrying out the process according to the invention, the reaction temperatures can be varied within a substantial range. In general, the process is carried out at temperatures between 0° C. and 100° C., preferably at temperatures between 10° C. and 60° C.

The process according to the invention is generally carried out under atmospheric pressure. However, it is also possible to carry out the process under increased or reduced pressure.

For carrying out the process according to the invention, between 1.0 and 2.0 moles, preferably between 1.1 and 1.5 moles, of hydrogen peroxide are generally employed per mole of starting compound of the formula (II).

The reactants are preferably reacted as follows: The sulphonylurea of the formula (II) is first mixed with the diluent, and the hydrogen peroxide is slowly metered into this mixture, with stirring. The reaction mixture is then stirred until the reaction is complete, if appropriate at elevated temperature. When the mixture has cooled it may be diluted with water, and the crystalline product is then isolated by filtration with suction.

If appropriate, salts can be prepared from the compounds of the general formula (I) according to the invention. Such salts are obtained in a simple manner by customary salt formation methods, for example by dissolving or dispersing a compound of the formula (I) in a suitable diluent such as, for example, methylene chloride, tert-butyl-methyl ether or toluene, and adding a suitable base. The salts can then be isolated by concentration or filtration with suction, if appropriate after prolonged stirring (cf. the Preparation Examples).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the crenera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of thi genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land and for the selective combating of weeds in annual cultures.

The compounds of the formula (I) according to the invention are particularly suitable for selectively combating monocotyledon and dicotyledon weeds in monocotyledon cultures, both by the preemergence and the postemergence method.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the f ormu.lations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and material phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable components for the mixtures are known herbicides, such as, for example, anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr; aryloxy-phenoxy-alkanoates such as, for example, diclofop-methyl, fenoxaprop-ethyl, fluazifop-butyl, haloxyfop-methyl and quizalofop-ethyl; azinones such as, for example, chloridazon and norflurazon; carbamates such. as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen, ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuronethyl, chlorsulfuron, cinosulfuron, metsulfuron-methyl, nicosulfuron, primisulfuron, pyrazosulfuron-ethyl, thifensulfuron-methyl, triasulfuron and tribenuronmethyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryne, terbutryne and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 10 g and 10 kg of active compound per hectare of soil surface, preferably between 50 g and 5 kg per ha.

The preparation and use of the active compounds according to the invention can be seen from the following examples.

PREPARATION EXAMPLES

EXAMPLE 1

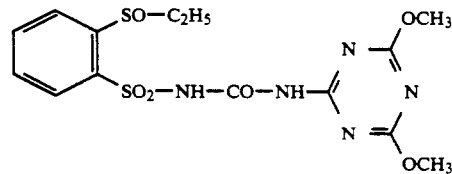

A mixture of 16 g (0.04 mol) of N-(4,6-dimethoxy-s-triazin-2-yl)-N'-(2-ethylthio-phenylsulphonyl)-urea, 70 ml of acetic acid and 6 ml of a 30% strength aqueous solution of hydrogen peroxide (0.06 mol of $H_2O_2$) is stirred for 18 hours at 22° C. After an addition of 120 ml of water, the product which has been obtained in the form of crystals is isolated by filtration with suction.

14 g (84% of theory) of N-(4,6-dimethoxy-s-triazin-2-yl)-N'-(2-ethylsulphinyl-phenylsulphonyl)-urea of melting point 165° C. are obtained.

Salts of compounds of the formula (I):

EXAMPLE 4a

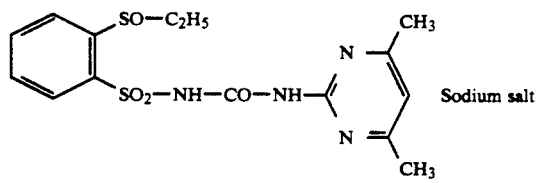

0.5 g (0.01 mol) of 80% sodium hydroxide powder is added, with stirring, to a mixture of 3.9 g (0.01 mol) of N-(4,6-dimethyl-pyrimidin-2-yl)-N'-(2-ethylsulphinyl-phenylsulphonyl)-urea and 100 ml of toluene. The mixture is stirred for 15 hours at 20° C.; the crystalline product is subsequently isolated by filtration with suction.

4.0 g (99% of theory) of the sodium salt of N-(4,6-dimethyl-pyrimidin-2-yl)-N'-(2-ethylsulphinyl-phenylsulphonyl)-urea of melting point 105° C. are obtained (with decomposition).

Other compounds of the formula (I) or their salts which can be prepared analogously to Example 1 or Example 4a and following the general description of the preparation process according to the invention are, for example, those mentioned in Table 1 below.

TABLE 1

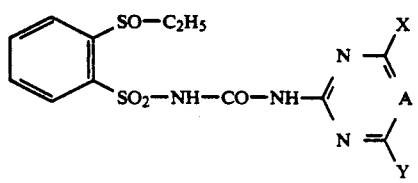
(I)

Examples of the compounds of the formula (I) and their salts

| Ex. No. | A | X | Y | Salt | Melting point (°C.) |
|---|---|---|---|---|---|
| 2 | N | OCH₃ | CH₃ | — | 109 |
| 3 | CH | OCH₃ | OCH₃ | — | 187 |
| 1a | N | OCH₃ | OCH₃ | sodium salt | 190 |
| 2a | N | OCH₃ | CH₃ | sodium salt | 200 |
| 3a | CH | OCH₃ | OCH₃ | sodium salt | 185 |
| 4 | CH | CH₃ | CH₃ | — | 135 |
| 5 | CH | OCH₃ | CH₃ | — | 182 |
| 5a | CH | OCH₃ | CH₃ | sodium salt | 148 |
| 6 | CH | Cl | OCH₃ | — | 204 |
| 6a | CH | Cl | OCH₃ | sodium salt | 155 |
| 7 | CH | Cl | OC₂H₅ | — | 148 |
| 7a | CH | Cl | OC₂H₅ | sodium salt | 80 |
| 8 | N | OCH₃ | OC₂H₅ | — | 167 |
| 8a | N | OCH₃ | OC₂H₅ | sodium salt | 137 |
| 9 | CH | H | CH₃ | — | 192 |
| 9a | CH | H | CH₃ | sodium salt | 170 |
| 10 | CH | OC₂H₅ | OC₂H₅ | — | 142 |
| 10a | CH | OC₂H₅ | OC₂H₅ | sodium salt | 110 |
| 11 | N | CH₃ | CH₃ | — | 146 |
| 11a | N | CH₃ | CH₃ | sodium salt | 170 |
| 12 | CH | C₂H₅ | OCH₃ | — | |
| 13 | CH | OC₂H₅ | CH₃ | — | |
| 14 | CH | OCH₃ | CF₃ | — | |
| 15 | N | OCH₃ | CF₃ | — | |
| 16 | N | OC₂H₅ | CH₃ | — | |
| 17 | N | C₂H₅ | OCH₃ | — | |
| 18 | CH | OCHF₂ | OCHF₂ | — | |
| 19 | CH | SCH₃ | CH₃ | — | |
| 20 | CH | SCH₃ | C₂H₅ | — | |
| 21 | N | SCH₃ | CH₃ | — | |
| 22 | CH | Cl | CH₃ | — | |
| 23 | N | SCH₃ | OCH₃ | — | |
| 24 | N | Cl | CH₃ | — | |

USE EXAMPLES

In the use examples which follow, the compounds mentioned below are used as comparison substances:

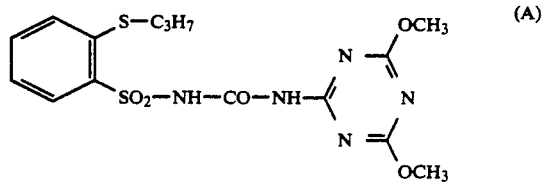
(A)

N-(4,6-dimethoxy-s-triazin-2-yl)-N'-(2-propylthio-phenylsulphonyl)-urea (disclosed in U.S. Pat. No. 4,818,277);

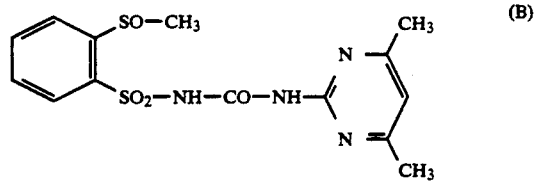
(B)

N-(4,6-dimethyl-pyrimidin-2-yl)-N'-(2-methylsulphinyl-phenylsulphonyl)-urea (disclosed in U.S. Pat. No. 4,169,719).

EXAMPLE A

Preemergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

A clearly superior activity compared with the prior art is shown, in this test, for example by the compounds of the following Preparation Examples: 2a, 3, 3a, 4, 4a, 5 and 5a.

EXAMPLE B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 1,000 l of water/ha. After three weeks, the degree of damage to the plants is rated in % damage in comparison to the development of the untreated control. The figures denote:

0% = no action (like untreated control)
100% = total destruction

A clearly superior activity compared with the prior art is shown, in this test, for example by the compounds of the following Preparation Examples: 1, 2 and 3.

It will be understood that the specification and examples are illustrative but not limitative of the present invention and that other embodiments within the spirit and scope of the invention will suggest themselves to those skilled in the art.

We claim:

1. An N-azinyl-N'-(2-ethylsulphinyl-phenylsulphonyl)urea of the formula

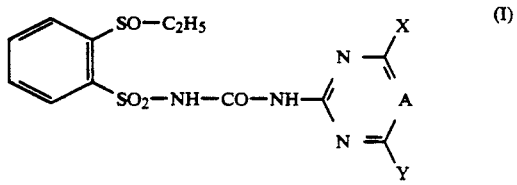

(I)

in which

A represents a CH group,

X represents hydrogen, halogen or alkyl, alkoxy or alkylthio, each of which has 1 to 3 carbon atoms and each of which is optionally substituted by halogen and Y represents alkyl or alkoxy, each of which has 1 to 3 carbon atoms and each of which is optionally substituted by halogen, or a salt thereof.

2. An urea according to claim 1 or a salt thereof, in which

A represents a CH group,

X represents hydrogen, fluorine, chlorine, bromine, or represents alkyl, alkoxy or alkylthio, each of which has 1 or 2 carbon atoms and each of which is optionally substituted by fluorine and/or chlorine, and Y represents alkyl or alkoxy, each of which has 1 or 2 carbon atoms and each of which is optionally substituted by fluorine and/or chlorine.

3. An urea according to claim 1 or a salt thereof, in which

A represents a CH group,

X represents hydrogen, chlorine, methyl, ethyl, methoxy, ethoxy, difluoromethoxy or methylthio and Y represents methyl, ethyl, trifluoromethyl, methoxy, ethoxy or difluoromethoxy.

4. The sodium salt of N-(4,6-dimethoxy-pyrimidin-2-yl)-N'-(2-ethylsulphinyl-phenylsulphonyl)-urea, of the formula

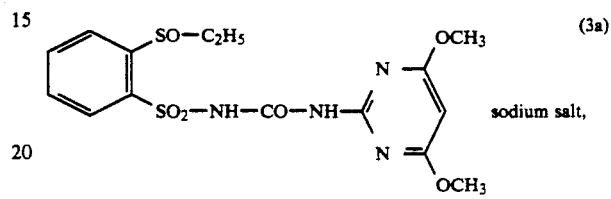

sodium salt, (3a)

according to claim 1.

5. A herbicidal composition comprising a herbicidally effective amount of an urea or a salt thereof according to claim 1 and a diluent.

6. A method of combating unwanted vegetation which comprises applying to such vegetation or to a locus from which it is desired to exclude such vegetation a herbicidally effective amount of an urea or salt thereof according to claim 1.

7. The method according to claim 6, wherein such compound is the sodium salt of N-(4,6-dimethoxy-pyrimidin-2-yl)-N'-(2-ethylsulphinyl-phenylsuphonyl)-urea.

* * * * *